United States Patent [19]
Ra et al.

[11] Patent Number: 6,090,384
[45] Date of Patent: *Jul. 18, 2000

[54] ANTIALLERGIC COMPOSTION

[75] Inventors: Chisei Ra, Chiba; Koji Naito; Minoru Hirama, both of Osaka; Ko Okumura, Chiba, all of Japan

[73] Assignees: Chisei RA, Chiba; Yoshitomi Pharmaceuticals Industries, Ltd., Osaka, Japan

[*] Notice: This patent issued on a continued prosecution application filed under 37 CFR 1.53(d), and is subject to the twenty year patent term provisions of 35 U.S.C. 154(a)(2).

This patent is subject to a terminal disclaimer.

[21] Appl. No.: 08/788,954

[22] Filed: Jan. 24, 1997

Related U.S. Application Data

[63] Continuation of application No. 08/474,188, Jun. 7, 1995, abandoned, which is a continuation of application No. 08/023,912, Feb. 26, 1993, abandoned.

[30] Foreign Application Priority Data

| Aug. 4, 1992 | [JP] | Japan | 4-229227 |
| Aug. 10, 1992 | [JP] | Japan | 4-213002 |
| Oct. 8, 1992 | [JP] | Japan | 4-270513 |
| Oct. 8, 1992 | [JP] | Japan | 4-270514 |
| Oct. 8, 1992 | [JP] | Japan | 4-270515 |

[51] Int. Cl.[7] .................................................. A61K 38/00
[52] U.S. Cl. .................................... 424/143.1; 424/125.1; 424/805; 424/810; 514/885
[58] Field of Search .................................. 424/805, 810, 424/125.1, 143.1; 514/885

[56] References Cited

U.S. PATENT DOCUMENTS

| 4,962,035 | 10/1990 | Leder et al. | 435/320 |
| 5,011,795 | 4/1991 | Levinson et al. | 435/69.2 |

FOREIGN PATENT DOCUMENTS

| 0457527 | 11/1991 | European Pat. Off. . |
| 457527 | 11/1991 | European Pat. Off. . |

OTHER PUBLICATIONS

*The Journal of Biological Chemistry*, vol. 266, No. 4 (1991), U. Blank et al., "Characterization of truncated a chain products from human, rat, and mouse high affinity receptor for immunoglobulin E" p.2639–2645.

*Nucleic Acids Research*, vol. 16, No. 8 (1988), J. Kochan et al., "Isolation of the gene coding for the alpha subunit of the human high affinity IgE receptor" p. 3584.

*Nucleic Acids Research*, vol. 13, No. 8 (1985), Andrea Riccio et al., "The human urokinase–plasminogen activator gene and its Promoter" p. 2759–2771.

*Biosci. Biotech. Biochem.*, vol. 56, No. 4 (1992), T. Yamaguchi et al., "Production of human antithrombin–III in a serum–free culture of CHO cells" p. 600–604.

M.C. Ray, et al., *J. Immunol.*, 131(3), 1096–1102 (1983).

U. Bland, et al., *J. Biol. Chem.*, 266(4), 2639–2646 (1991).

C. Ra, et al., *International Immunology*, 5(1), 47–54 (1993).

*Primary Examiner*—Laurie Scheiner
*Attorney, Agent, or Firm*—Sughrue, Mion, Zinn, Macpeak & Seas, PLLC

[57] ABSTRACT

Disclosed is an antiallergic composition comprising, as an active ingredient, a peptide which is capable of binding to human IgE, more specifically the high-affinity immunoglobulin E receptor α chain or a soluble fragment, which is capable of binding to human IgE, or the high-affinity immunoglobulin E receptor α chain. The composition is clinically useful for blocking allergic responses.

7 Claims, 3 Drawing Sheets

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
      (A) LENGTH: 591 base pairs
      (B) TYPE: nucleic acid
      (C) STRANDEDNESS: double
      (D) TOPOLOGY: linear

```
    (ii) MOLECULE TYPE: DNA (genomic)

(vi) ORIGINAL SOURCE:
         (A) ORGANISM: Homo sapiens (ix) FEATURE:
         (A) NAME/KEY: CDS
         (B) LOCATION: 1..591

(xi) SEQUENCE DESCRIPTION: SEQ ID NO:1:

ATG GCT CCT GCC ATG GAA TCC CCT ACT CTA CTG TGT GTA GCC TTA CTG      48
Met Ala Pro Ala Met Glu Ser Pro Thr Leu Leu Cys Val Ala Leu Leu
 1               5                  10                  15

TTC TTC GCT CCA GAT GGC GTG TTA GCA GTC CCT CAG AAA CCT AAG GTC      96
Phe Phe Ala Pro Asp Gly Val Leu Ala Val Pro Gln Lys Pro Lys Val
                20                  25                  30

TTC TTG AAC CCT CCA TGG AAT AGA ATA TTT AAA GGA GAG AAT GTG ACT     144
Phe Leu Asn Pro Pro Trp Asn Arg Ile Phe Lys Gly Glu Asn Val Thr
            35                  40                  45

CTT ACA TGT AAT GGG AAC AAT TTC TTT GAA GTC AGT TCC ACC AAA TGG     192
Leu Thr Cys Asn Gly Asn Asn Phe Phe Glu Val Ser Ser Thr Lys Trp
        50                  55                  60

TTC CAC AAT GGC AGC CTT TCA GAA GAG ACA AAT TCA AGT TTG AAT ATT     240
Phe His Asn Gly Ser Leu Ser Glu Glu Thr Asn Ser Ser Leu Asn Ile
 65                  70                  75                  80

GTG AAT GCC AAA TTT GAA GAC AGT GGA GAA TAC AAA TGT CAG CAC CAA     288
Val Asn Ala Lys Phe Glu Asp Ser Gly Glu Tyr Lys Cys Gln His Gln
                 85                  90                  95

CAA GTT AAT GAG AGT GAA CCT GTG TAC CTG GAA GTC TTC AGT GAC TGG     336
Gln Val Asn Glu Ser Glu Pro Val Tyr Leu Glu Val Phe Ser Asp Trp
                100                 105                 110

CTG CTC CTT CAG GCC TCT GCT GAG GTG GTG ATG GAG GGC CAG CCC CTC     384
Leu Leu Leu Gln Ala Ser Ala Glu Val Val Met Glu Gly Gln Pro Leu
            115                 120                 125

TTC CTC AGG TGC CAT GGT TGG AGG AAC TGG GAT GTG TAC AAG GTG ATC     432
Phe Leu Arg Cys His Gly Trp Arg Asn Trp Asp Val Tyr Lys Val Ile
        130                 135                 140

TAT TAT AAG GAT GGT GAA GCT CTC AAG TAC TGG TAT GAG AAC CAC AAC     480
Tyr Tyr Lys Asp Gly Glu Ala Leu Lys Tyr Trp Tyr Glu Asn His Asn
145                 150                 155                 160

ATC TCC ATT ACA AAT GCC ACA GTT GAA GAC AGT GGA ACC TAC TAC TGT     528
Ile Ser Ile Thr Asn Ala Thr Val Glu Asp Ser Gly Thr Tyr Tyr Cys
                165                 170                 175

ACG GGC AAA GTG TGG CAG CTG GAC TAT GAG TCT GAG CCC CTC AAC ATT     576
Thr Gly Lys Val Trp Gln Leu Asp Tyr Glu Ser Glu Pro Leu Asn Ile
                180                 185                 190

ACT GTA ATA AAA GCT                                                 591
Thr Val Ile Lys Ala
        195

(2) INFORMATION FOR SEQ ID NO:2:

(i) SEQUENCE CHARACTERISTICS:
         (A) LENGTH: 197 amino acids
         (B) TYPE: amino acid
         (D) TOPOLOGY: linear (ii) MOLECULE TYPE: protein (xi) SEQUENCE DESCRIPTION: SEQ ID NO:2:

Met Ala Pro Ala Met Glu Ser Pro Thr Leu Leu Cys Val Ala Leu Leu
 1               5                  10                  15
```

-continued

```
Phe Phe Ala Pro Asp Gly Val Leu Ala Val Pro Gln Lys Pro Lys Val
            20                  25                  30

Phe Leu Asn Pro Pro Trp Asn Arg Ile Phe Lys Gly Glu Asn Val Thr
            35                  40                  45

Leu Thr Cys Asn Gly Asn Asn Phe Phe Glu Val Ser Ser Thr Lys Trp
        50                  55                  60

Phe His Asn Gly Ser Leu Ser Glu Glu Thr Asn Ser Ser Leu Asn Ile
65                      70                  75                  80

Val Asn Ala Lys Phe Glu Asp Ser Gly Glu Tyr Lys Cys Gln His Gln
                85                  90                  95

Gln Val Asn Glu Ser Glu Pro Val Tyr Leu Glu Val Phe Ser Asp Trp
            100                 105                 110

Leu Leu Leu Gln Ala Ser Ala Glu Val Val Met Glu Gly Gln Pro Leu
        115                 120                 125

Phe Leu Arg Cys His Gly Trp Arg Asn Trp Asp Val Tyr Lys Val Ile
            130                 135                 140

Tyr Tyr Lys Asp Gly Glu Ala Leu Lys Tyr Trp Tyr Glu Asn His Asn
145                     150                 155                 160

Ile Ser Ile Thr Asn Ala Thr Val Glu Asp Ser Gly Thr Tyr Tyr Cys
                165                 170                 175

Thr Gly Lys Val Trp Gln Leu Asp Tyr Glu Ser Glu Pro Leu Asn Ile
            180                 185                 190

Thr Val Ile Lys Ala
            195
```

ANTIALLERGIC COMPOSTION

This is a Continuation of Application No. Ser. 08/474,188 filed Jun. 7, 1995, now abandoned, which is a continuation of application Ser. No. 08/023,912, filed Feb. 26, 1993, now abandoned.

FIELD OF THE INVENTION

The present invention relates to compositions containing, methods of producing and methods of using peptides which are capable of binding to human immunoglobulin E (IgE). More particularly, the invention relates to a prophylactic and/or therapeutic composition for allergic diseases which comprises a high affinity immunoglobulin E receptor α-chain (FcεRIα) or a soluble fragment of such a high affinity immunoglobulin E receptor α-chain, which is capable of binding to human IgE.

BACKGROUND OF THE INVENTION

Type I allergy is an inflammatory response which is elicited as the invasion of exogenous agents into the body triggers the release of various enzymes and chemical mediators, such as histamine and leukotrienes, from mast cells and eosinophils, which in turn induce tissue-damaging inflammations. The allergic response, when generalized, can lead to a systemic and often life threatening reaction known as anaphylactic shock.

The agents which trigger an anaphylactic shock response include various drugs, such as penicillin and insulin, sources of desensitizing allergens such as ticks and fungi, dietary allergens such as eggs and peanuts, iodine-containing contrast media, local anesthetics and so on.

The current pharmacotherapy for anaphylactic shock consists of the administration of epinephrine and steroids. It is reported that if early therapy is judiciously instituted, the prognosis for this condition is generally satisfactory. However, these current treatments are no more than symptomatic remedies and the prophylaxis of anaphylactic shock is considered to be truly important. However, there is no established prophylactic modality for anaphylactic shock, and the current clinical practice appears to be based, at best, on the vague concept of preventing the invasion of high-risk foreign agents.

Therefore, in patients requiring certain drugs, such as penicillin and other antibiotics, and in cases in which an iodine contrast medium is used in X-ray diagnosis, these agents are administered of necessity, despite the attendant risk of anaphylactic shock. Thus, there is a pressing need for a positive prophylactic measure against such vigorous immune system responses.

In pollen allergy, symptoms occur preferentially in the nose and eye. Recent years have witnessed a rapid increase in the number of patients who complain of the so-called pollinosis syndrome due to pollens of cedar and other allergenic plants, resulting in, for example, allergic conjuctivitis and allergic rhinitis (eye watering, sinus congestion, nasal congestion, sneezing and the like).

For the prevention of pollen disease, a prophylactic treatment with antiallergic agents, a symptomatic treatment with antihistamines and steroids, and hyposensitization therapy are generally indicated at present.

However, there is not available as yet an antiallergic agent effective enough as a preventive drug, and the antihistamines and steroids in current use for symptomatic treatment have the problem of side effects.

Atopy provides hereditary basis for allergic responses. The condition is revealed as a congenital hypersensitivity to specific agents and is usually manifested as bronchial asthma and allergic rhinitis in the patient and his family.

Atopic dermatitis is an inflammatory disease of the skin, which may arise because of a predisposition and which is often characterized by areas of localized itch. It is also known that as the affected area is scratched, the local eruption can be aggravated so that the disease runs a chronic course. Moreover, the pruritus associated with atopic dermatitis develops suddenly in many cases and tends to be provoked and intensified by the slightest stimulation.

A variety of treatments have been attempted for atopic dermatitis, but they have proved unsuccessful. The current therapeutic modality for this disease consists of the topical treatment primarily with topical adrenocorticoids and, as an adjunct therapy, antipruritic agents such as antihistamines. But since these drugs are not free from side effects, the advent of a safe and more sure-acting drug for the prevention and treatment of atopic dermatitis has been awaited in earnest.

Patients with bronchial asthma are rapidly increasing in number and present a serious problem everywhere in the world today. Bronchial asthma is an airway disease, the cardinal manifestation of which is respiratory distress due to paroxysmal airway constriction, which is life-threatening at times.

While many etiologic agents are usually involved in the onset of bronchial asthma, the chief cause is generally believed to be an increased airway responsiveness due to allergic factors associated with inhaled antigens such as ticks, pollen, dust and so on.

For the treatment of bronchial asthma, prophylaxis with antiallergic drugs and symptomatic treatment with β-receptor stimulants and steroids is practiced today, but there is no antiallergic drug effective enough as a prophylactic. Further, the problem of side effects has been pointed out frequently with the use of β-receptor stimulants and steroids used for symptomatic treatment.

A high affinity immunoglobulin E receptor (FcεRI) is a glycoprotein having a tetrameric structure consisting of an α-chain, a β-chain and two disulfidized γ-chains. It has been reported that a soluble fragment of FcεRI α-chain (sFcεRIα) is produced by a genetic engineering techniques using DHFR-deficient CHO cells and that only the extracellular region of the α-chain is involved in the high-affinity binding to IgE [Blank, U. et al., J. Biol. Chem., 266, 2639 (1991)].

SUMMARY OF THE INVENTION

The object of the present invention is to provide a clinically useful antiallergic composition which arrests allergic reactions at the rudiment.

The inventors of the present invention have found after much research directed to the above object that the prophylactic administration of a peptide which is capable of binding to human IgE inhibits the onset of allergic diseases. Further, the administration of such a peptide which is capable of binding to human IgE even after development of allergic diseases results in improvement of allergic symptoms. Furthermore, it has been found that in gene amplification using a dihydrofolate reductase (DHFR) gene for the production of sFcεRIα the use of a urokinase (UK) promoter for controlling the expression of the DHFR gene increase an gene amplification level much higher than the prior art level. The present invention based on the above findings.

Having been developed on the basis of the above findings, the present invention relates to an antiallergic composition containing a peptide which is capable of binding to human IgE and to a method of producing sFCεRIα which is comprises transfecting an animal cell with a plasmid (1) carrying a DNA coding for sFCεRIα with a promoter capable of controlling the expression thereof in animal cells and a DHFR gene with a UK promoter or transfecting an animal cell with both a plasmid (2) carrying a DNA coding for sFCεRIα with a promoter capable of controlling the expression thereof in animal cells and a plasmid (3) carrying a DHFR gene with a UK promoter, and culturing the animal cells.

DETAILED DESCRIPTION OF THE INVENTION

The term "peptide which is capable of binding to human IgE" as used herein means a peptide which specifically binds to human IgE to inhibit its function. Any peptide is usable in the present invention as long as it show about 80% IgE inhibition in the IgE inhibition assay as described below. Specific examples include a peptide containing a high affinity immunoglobulin E receptor α-chain (FcεRIα) and a peptide containing a soluble fragment of such a high affinity immunoglobulin E receptor α-chain (sFcεRIα) which are capable of binding to human IgE.

The above-mentioned peptides inhibit the binding of IgE to the high affinity immunoglobulin E receptor (FcεRI) which specifically binds to the Fc moiety of IgE, on the cell membranes of mast cells and eosinophils and, therefore, arrest allergic reactions at the source.

FcεRIα stands for the α-chain of said FcεERI, and sFcεRIα stands for the extracellular region of the α-chain.

A peptide which is capable of binding to human IgE for use in the present invention, need only contain at least the extracellular region of the α-chain, viz. sFcεRIα, and both FcεRIα and FcεRI may likewise be employed with success. Mutants artificially derived by a genetic engineering technique and a derivative for drug delivery system, for example the conjugate with albumin, can also be used if the mutant is capable of binding to human IgE, but sFcεRIα is particularly desirable. Preferably, the peptides are obtained and derived from humans.

sFcεRIα can be produced by tissue culture or by genetic engineering. The process for producing sFCεRIα according to the present invention are described in detail below.

[I] Plasmid (1)

Plasmid (1) carrying a DNA coding for sFCεRIα with a promoter capable of controlling the expression thereof in animal cells and a DHFR gene with a UK promoter can be prepared by inserting (i) a DNA conding for sFCεRIα with a promoter capable of controlling the expression thereof in animal cells upstream therefrom and (ii) a DHFR gene with a UK promoter upstream therefrom into a plasmid. Plasmid (1) is constructed so that a DNA coding for a heterologous protein, sFCεRIα, functions under the control of a promoter capable of controlling the expression thereof in animal cells. Examples of such a promoter include a promoter of polyoma, adenovirus 2 or, in most cases, simian virus 40 (SV40) origin. The early or late promoter of SV40 is particularly useful since they can be obtained readily from the virus as a fragment containing the replication origin of SV40 [Fiers et al., Nature, 273, 113 (1978)]. A DNA fragment of SV40 about 250 bp containing from the HindIII site to the BglI site in the replication origin can be also used. Further, any promoter and regulatory sequence (enhancer) related to the heterologous protein gene can also be used as long as they function in a host cell.

Usable as a promoter-enhancer to be used in the expression vectors for use in animal cells are the promoter-enhancer of the SV40 early or late gene, the adenovirus 2 major later promoter region, the globulin enhancer-promoter region, the LTR of RNA viruses, the metallothionein promoter region, the β-actin promoter and the like. As for the origin of replication, one derived from SV40 or some other virus (e.g. polyoma, adeno, VSV, BPV) may be inserted into the vector employed, or the replication mechanism of the host cell chromosome may be used. If the vector is integrated into the host cell chromosome, the latter is enough.

Further, plasmid (1) is constructed so that a DHFR gene functions under the control of the UK promoter added upstream therefrom. Both of the UK promoter and the DHFR gene are known. The former is described in Nucl. Acids Res., 13, 2759–2771 (1985), etc. and the latter is described in JP-A-59-192089, JP-A-63-105675, etc. (the term "JP-A" used herein means un unexamined published Japanese patent application).

Any human sFcεRIε can be used as long as it exhibits activity of the high affinity immunoglobulin E receptor. An example of a DNA coding for human sFcεRIα is one described in Kochan et al., Nuclec Acids Res., 16, 3584 (1988).

In plasmid (1), a unit of a DNA coding for human sFcεRIα and a promoter capable of controlling the expression thereof in animal cells and a unit of the DHFR gene and the UK promoter may be inserted in the same direction or in the reverse direction. Plasmid (1) may further contain the replication origin, the ribosome-binding site or the RNA splicing site upstream from a DNA unit of a DNA coding for human sFcεRIα and a promoter capable of controlling the expression thereof in animal cells, the polyA addition site or the transcription termination sequence downstream from the DNA unit.

[II] Plasmids (2) and (3)

Plasmid (2) contains a DNA coding for human sFcεRiα and a promoter capable of controlling the expression thereof in animal cells and plasmid (3) contains the DHFR gene and the UK promoter. These plasmids contain the same DNA unit as described in the above [I]-(i) and (ii), respectively and are used to cotransfect animal cells for the expression of human sFcεRIα.

[III] Transfectants

Transfectants according to the present invention can be obtained by transfecting animal cells with plasmid (1) described in the above [I] or cotransfecting animal cells with plasmids (2) and (3) as described in the above [II]. Usable as the animal cell line are Green monkey kidney cell line (VERO), HeLa cells, Chinese hamster ovary (CHO) cell line, W138, new-born hamster kidney cell line (BHK), CV-1 Origin SV40 cell (COS-7), MDCK cell line, C127, HKG, human kidney cell line and the like. Specific examples thereof include CHO-K1 (ATCC CCL61), BHK (ATCC CCL10), COS-7 (ATCC CRL1651), VERO (ATCC CCL81), among others. Particularly preferred are those cells deficient in the DHFR gene.

Transfection of animal cells can be carried out by the conventional method such as calcium phosphate precipitation method, protoplast polyethylene glycol fusion method, electropolation or the like.

DNA amplification using methotrexate (MTX) can be carried out by culturing the transfectants in a medium containing MTX in a concentration of 10 $\mu$M to 10 $\mu$M and selecting the MTX resistant cells from the cells which can grow in the medium. MTX may be added stepwise to the medium or added in a high concentration in a single step.

Examples of the medium include MEM-α supplemented with 1 to 10% fetal calf serum (FCS), Dulbecco's modified MEM (D-MEM) and the like. Cultivation of the transfectants can be carried out at 10 to 37° C. for 1 to 200 hours.

[IV] Production of heterologous protein

The transfectants described in the above [III] are cultivated to cause expression of human sFcεRIα gene by the known methods.

The production of sFcεRIα by genetic engineering may be carried out using *E. coli* or yeasts instead of the above-mentioned animal cells.

The polypeptides of the present invention can be obtained by art-recognized methods, for example, cell lysis and purification or mere purification from the culture medium in those instances in which secretion has occurred. Standard purification methods can be used, such as chromatography, dialysis, affinity chromatography, combinations thereof, and the like. A particularly suitable method is affinity chromatography wherein an IgE antibody is affixed to a chromatography matrix. The solution containing the target polypeptides is passed over the matrix and bound molecules, including the target protein, are eluted from the matrix, for example, by using high ionic strength buffer.

The peptide which is capable of binding to human IgE can be applied as a systemic therapy or as a topical therapy.

For systemic treatment, the peptide is dissolved in physiological saline for injection or distilled water for injection and administered parenterally, preferably intravenously. The dosage form may be a liquid or a lyophilizate and can be manufactured by methods well known in the art.

For topical administration, various dosage forms for external application to the skin or mucosa such as ocular mucosa, nasal mucosa, bronchial mucosa, etc., can be utilized.

The antiallergic composition of the present invention can also be administered in other dosage forms and routes of administration, chosen according to the type of allergy to be prevented or treated.

For the prevention or therapy of pollen allergy, ophthalmic and nasal solutions or ointments may prove of benefit. Any such pharmaceutical preparations can be manufactured by known manufacturing methods.

For example, an ophthalmic or nasal solution can be manufactured by dissolving the active ingredient peptide which is capable of binding to human IgE in distilled water for injection, adding any auxiliary agent required, such as a buffer, isotonizing agent, thickener, preservative, stabilizer, surfactant, antiseptic, etc., and adjusting the mixture to pH 4 to 9. A nasal spray can be manufactured for example by the method described in JP-A-63-101318.

The ointment which may be used in the present invention is preferably a gel ointment. Such an ointment can be manufactured, for example, by mixing the active ingredient peptide which is capable of binding to human IgE with a gel base prepared by using a carboxyvinyl polymer and, as a basic thickener, sodium hydroxide or the like and, after addition of auxiliary agents as necessary, adjusting the mixture to pH 4 to 9.

The topical dermatologic preparation for the prophylaxis and/or therapy of atopic dermatitis includes, a cream, a gel ointment and a lotion. Any of these preparations can be manufactured by using the peptide which is capable of binding to human IgE in combination with a water-soluble high molecular compound, an oil, white petrolatum, a lower alcohol or the like. If necessary, auxiliary agents such as a buffer, isotonizing agent, thickener, preservative, stabilizer, surfactant, lubricant, preservative and so on, may be added.

A prophylactic-therapeutic composition for bronchial asthma can be prepared in a dosage form which is suitable for topical application to the bronchial mucosa or nasal mucosa. A typical procedure comprises dissolving the peptide of the invention in an appropriate solvent such as physiological saline and injectable solutions and packing the peptide solution into a spray device for aerosol inhalation.

The composition can be used for both prophylaxis and for symptomatic control. The dosage is dependent on the type of disease and the patient's age, sex and condition. In normal human serum, IgE circulates at a concentration of about 3 ng/ml, which is based on a molecular weight of 185,000, corresponding to about $10^{10}$ IgE molecules per ml of serum. In serum of patients suffering from allergic diseases, the IgE concentration raises to 100 to 10,000 times as high as that in normal human serum. For example, the IgE concentration in serum of patients suffering from hay fever, allergic rhinitis or atopic asthma is about 300 ng/ml ($10^{12}$ molecules/ml), and that in atopic dermatitis patients is about 30 $\mu$g/ml ($10^{14}$ molecules/ml). For prophylactic treatment, it is preferable to administer at least twice the amount of the peptide of the present invention needed for binding the amount of IgE increase caused by the exogenous factor. For symptomatic control, it is preferable to use a massive dose soon after onset, preferably at least 10-fold as great a dose relative to the amount of IgE increased cause by the exogenous factor. In view of the following Test Example 5, the dosage for the therapeutic purpose is considered preferably not less than 500 $\mu$g/kg.

For use as a prophylactic treatment for anaphylactic shock, the peptide of the present invention may be administered once or twice a day beginning several days, e.g., 4 days, prior to administration of a sensitizing drug or contrast medium.

The following reference, test, and working examples illustrate the invention in further detail. However, they are not to be construed as limiting the scope of the invention.

EXAMPLE 1

Production of sFcεRIα

[I] Construction of FcεRI/pKC3

[Construction of a plasmid using a DNA coding for the sFcεRIα chain with a promoter (SV40) capable of controlling the expression of said chain in an animal cell]

Figure 1:
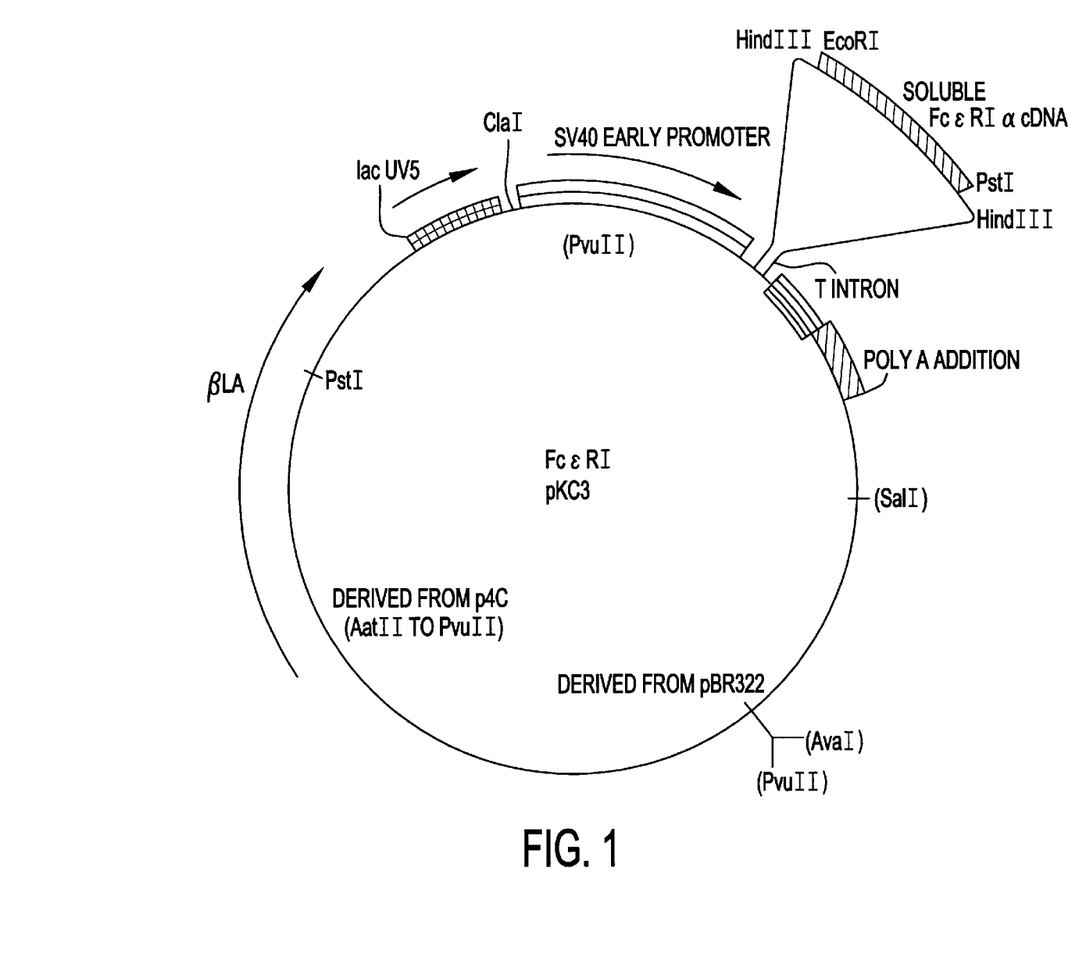
FIG. 1 illustrates the structure of the plasmid designated as FcεRI/pKC3.

A plasmid, FcεRIα/pKC3 (FIG. 1), containing the human FcεRIα chain leader sequence and the human sFcεRIα chain gene as incorporated in pKC3 was constructed as described in Blank et al. [J.Biol. Chem., 266, 2639 (1991)]. The DNA sequence of the human sFcεRIα chain-encoding gene as well as the amino acid sequence deduced therefrom is shown in SEQ ID: 1 (Nucleic Acids Research, 16(8), 3584 (1988)).

[II] Construction of pTT06

[Construction of a plasmid using a DNA coding for dihydrofolate reductase (DHFR) with the urokinase (UK) promoter]

Figure 2:
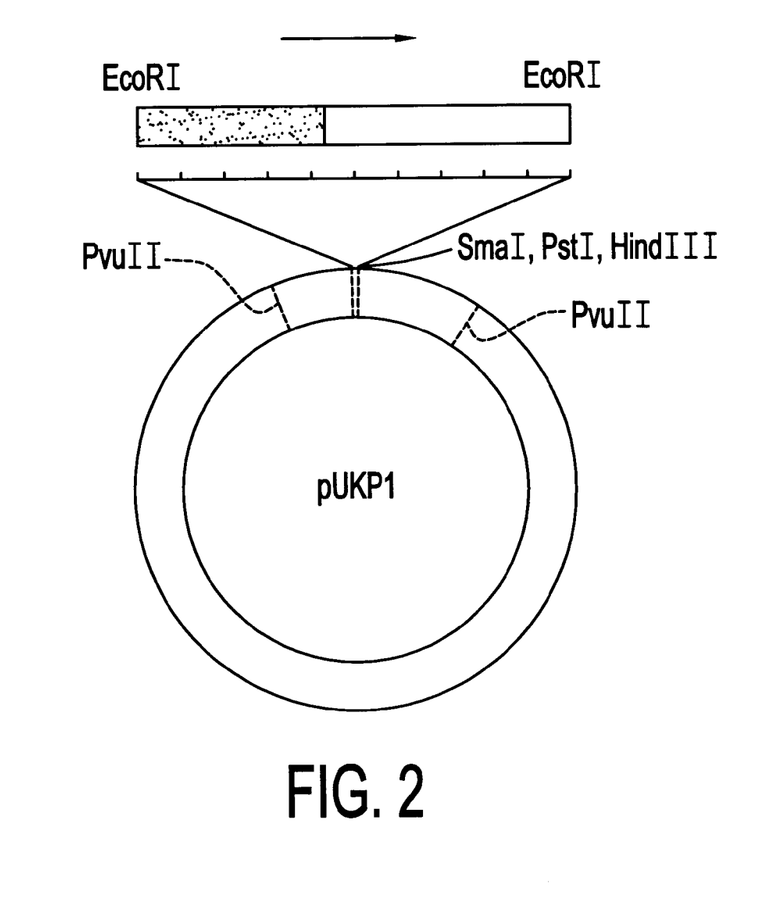
FIG. 2 illustrates the structure of the subcloned pUKP1.

A plasmid, pTT06, containing the UK promoter, DHFR cDNA and SV40 poly(A) was constructed as described below in accorcance with the method described in Biosci. Biotech. Biochem., 56 (4), 600–604 (1992) (cf. FIG. 2).

(i) Construction of pUKP-1: preparation of DNA encoding UK promoter (1) Preparation of probe Plasmid pUK4 containing a part of human urokinase cDNA (JP-A-61-177987) was digested with PstI and about 400 bp DNA fragment was isolated by 1% agarose gel electrophoresis followed by electroelution. A 0.4 μg portion of this fragment was labeled with [α-$^{32}$P]dCTP (Amersham, PB10205) using MultiPrime Kit (Pharmacia).

```
DNA fragment 0.4 μg (8 μl)
    ↓ ←   heating at 100° C. for 3 min. and
    ↓     cooling rapidly on ice water bath
    ↓ ←   adding 15 μl of MultiPrime soln. 1
    ↓ ←   adding 25 μl (250 μCi) of [α-$^{32}$P]dCTP
    ↓ ←   adding 2 μl of MultiPrime soln. 2
    ↓ ←   incubating at room temperature for
    ↓     1.5 hours
    ↓ ←   applying the mixture onto a NICK
    ↓     Column (Pharmacia) equilibrated with
    ↓     a buffer containing 0.1% SDS, 1 mM
    ↓     EDTA, 10 mM Tris-HCl, pH 7.4
    ↓ ←   fractionating the eluate in a volume
    ↓     of 100 μl portions
```

The desired fractions were combined and measured for Cerenkov count and it was found that the Cerenkov count was $9.69 \times 10^7$ cpm. The labeling efficiency and specific radioactivity were calculated as 41% and $2.4 \times 10^8$ cpm/μg, respectively.

(2) Southern hybridization of DNA derived from HKG cells

According to Riccio et al., Nucl. Acids Res., 13, 2759–2771 (1985), the human urokinase promoter region is obtained as a 5.8 kb EcoRI fragment and a 12 kb BamHI fragment from human chromosomal DNA. A DNA of HKG cells was digested independently with EcoRI and BamHI. A 10 μg portion of each digests was subjected to 0.8% agarose gel electrophoresis followed by the Southern hybridization using the probe prepared in the above (1). As a result, a signal was detected at the position corresponding to each of the desired fragment sizes.

(3) Preparation of 5.8 kb EcoRI fragment

200 μg of high molecular weight DNA of HKG cell was digested with 1,000 units of EcoRI overnight at 37° C. The resulting digests were subjected to 0.8% agarose gel electrophoresis (Electrophoretic device HE-12, Takara Shuzo) using λ-DNA digested with HindIII as a marker and the gel was stained with ethidium bromide. The gel was excised in a length of 2 mm around the position corresponding to 5.8 kb. The upper and lower parts thereof were also excised in a length of 3 mm. The resulting gel portions were subjected to electroelution to extract DNA fragments. A part of the extracted DNA fragments was subjected to 0.8% agarose gel electrophoresis followed by the Southern hybridization in order to confirm as to whether or not the desired DNA fragments were included in the extracted NA fragments. As a result, it was assumed that the DNA fragment extracted from the gel of 2 mm around the 5.8 kb position contained the desired urokinase promoter region.

(4) Preparation of DNA library and screening

DNA library of the DNA extracted in the above (3) was prepared using phage vector λgt10. A total of $6.5 \times 10^5$ recombinant phages were subjected to primary screening by plaque hybridization. As a result, 28 positive clones were obtained. The positive clones were subjected to secondary screening to thereby obtain 5 positive clones. DNA was extracted from the recombinant phages which gave positive clones by the simplified extraction method. The extracted DNA was digested with EcoRI and the digests were subjected to 1% agarose gel electrophoresis followed by the Southern hybridization. The results of the Southern hybridization revealed that two recombinant phages were positive.

(5) Subcloning of 5.8 kb EcoRI fragment

A phage DNA was extracted from the clone, which was confirmed to be positive by the Southern hybridization, by the simplified extraction method. The extracted DNA was digested with EcoRI and the digests were extracted with phenolchloroform. The aqueous layer was further extracted with chloroform and the extract was precipitated with ethanol. The resulting phage DNA fragments digested with EcoRI were ligated with a 1 μg portion of the pUC9 (Pharmacia) which was digested with EcoRI and subsequently treated with alkaline phosphatase. The resulting ligation products were used to transform E. coli HB101. Some of the transformed cells were subjected to the simplified extraction method to extract plasmid DNA, which was digested with EcoRI and electrophoresed on 1% agarose gel. As a result, it was found that several subclones contained a 5.8 kb DNA fragment. Two clones were digested with various restriction enzymes and the digests were subjected to 1% agarose gel electrophoresis. These clones showed different cleavage sites, but contained several identical fragments. Thus, it was assumed that the 5.8 kb DNA fragment was inserted into the respective clones in the different directions. These plasmids were named as pUKP1 (FIG. 2) and pUKP2, respectively.

(6) Digestion of pUKP1 with restriction enzymes

It was examined as to whether or not pUKP1 contained the DNA fragments expected to be contained in view of the restriction enzyme cleavage map deduced from the base sequence of human urokinase reported by Riccio et al (supra).

E. coli HB101 carrying pUKP1 was cultured in 100 ml of Superbroth containing 40 μg/ml of ampicillin overnight at 37° C. and the plasmid DNA was isolated from the cells by the alkali-SDS method. The thus obtained plasmid DNA was subjected to digestion with various restriction enzymes. Table 1 shows the DNA fragments expected to be contained in pUKP1, sizes of the fragments, and the presence or absence of the fragments. As shown in Table 1, all the expected fragments were found in pUKP1. Therefore, it was confirmed that the DNA fragment coding for the desired human urokinase promoter region was cloned.

TABLE 1

| Restriction enzyme | Size of fragment (bp) | Presence or absence of fragment |
|---|---|---|
| BglII | 270 | 0* |
| SmaI | 2266 | 0 |
| PvuII | 695 | 0 |
|  | 1641 | 0 |
|  | 792 | 0 |
| PstI | 682 | 0 |
|  | 946 | 0 |
|  | 584 | 0 |
| HindIII | 1817 | 0 |
| SmaI + EcoRV | 590 | 0 |
| EcoRI + EcoRV | 3050 | 0 |
| HindIII + EcoRV | 1283 | 0 |
| BamHI + BglII | 595 | 0 |
| BglII + EcoRV | 2205 | 0 |

*Note: 0 means that the presence of the expected fragment.

(7) Confirmation of a part of the base sequence fragment.

A part of the base sequence of the sequence of pUKP1 in the above (6) was determined by the dideoxy method. As a result, the base sequence thus determined was in agreement with that reported by Riccio et al (supra).

Construction of pTT06
[Construction of plasmid containing UK promoter, DHFR cDNA and SV40 polyA]

Figure 3:
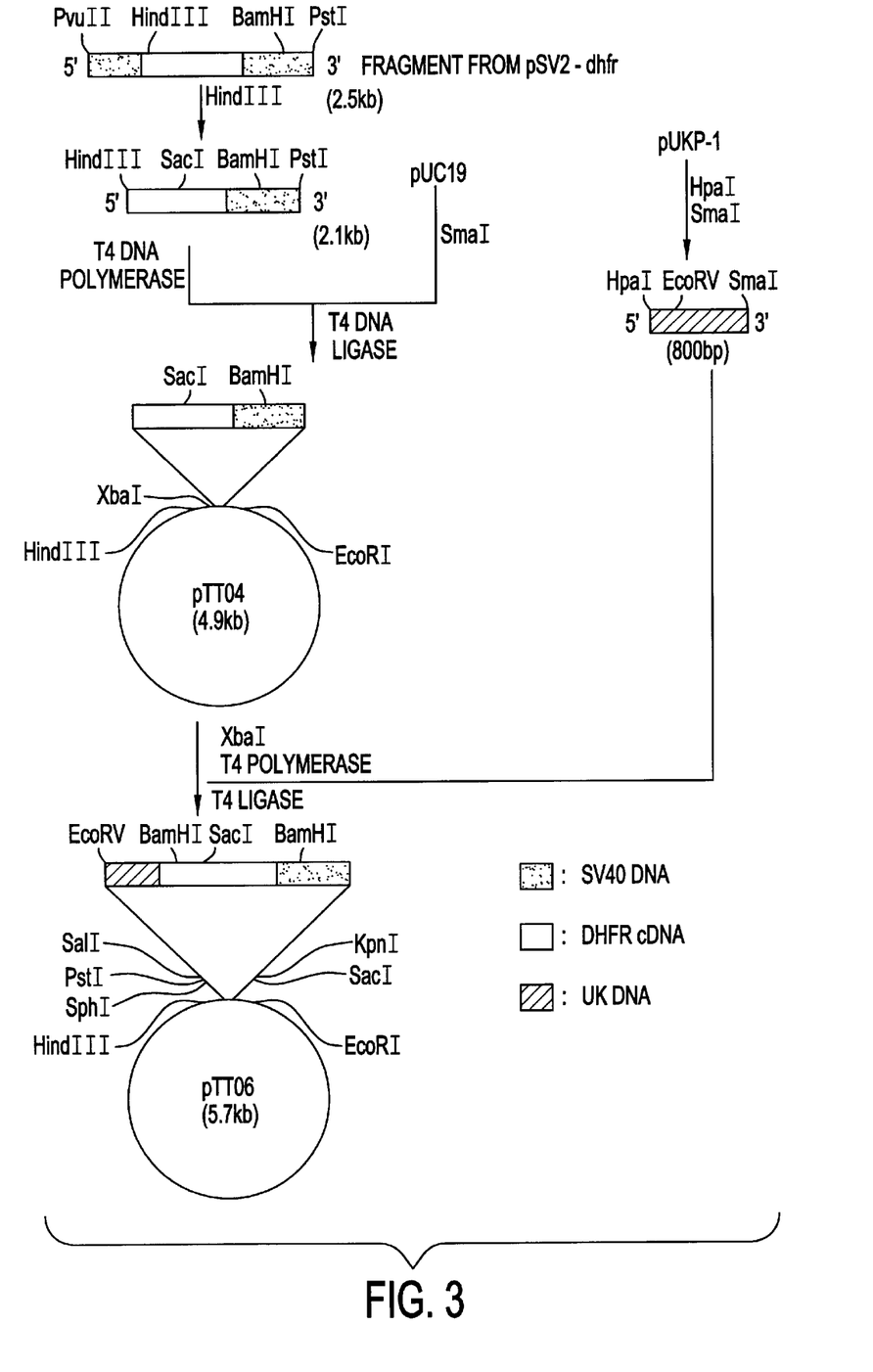
FIG. 3 illustrates the scheme for constructing the plasmid designated as pTT06.

Plasmid pTT06 was constructed in the following manner (FIG. 3).

pSV2-dhfr (JP-A-63-105675) was digested with PvuII and PstI to obtain a DNA fragment of 2.5 kb containing SV40 enhancer-promoter, DHFR cDNA and SV40 late polyA addition signal. The resulting DNA fragment was further digested with HindIII so as to delete the SV40 enhancer-promoter region. The thus obtained HindIII-PstI fragment of 2.1 kb was treated with T4 DNA polymerase to render the both ends blunt and inserted into the SmaI site of pUC19 (Takara Shuzo) for cloning. pTT06 thus obtained contained DHFR cDNA in such a manner that the 5' end (the N terminal of the protein) of DHFR cDNA was joined to the HindIII site of the pUC19 polylinker. In order to examine as to whether or not PTT04 was a desired plasmid, pTT04 was digested with BamHI to give a DNA fragment of from the BamHI site in the pUC19 polylinker to the BamHI site downstream from the SV40 late polyA addition signal. Thus, a DNA fragment of 1.6 kb was obtained. Then, pUKP-1 was digested with HpaI and SmaI to obtain a DNA fragment of about 800 bp containing from the SmaI site at about 30 bp downstream from the transcription initiation site of the urokinase gene to the HpaI site at about 800 bp upstream from the transcription initiation site. This DNA fragment containing the UK promoter was inserted into the upstream site of DHFR cDNA. Namely, pTT04 was digested with XbaI and the digestion product was treated with bacterial alkaline phosphatase (BAP) and then blunt-ended with T4 DNA polymerase. The resulting fragment was ligated with the HpaI-SmaI fragment containing the UK promoter. After transformation, the clones in which the DHFR gene and the UK promoter were inserted in the same transcription direction were selected. Subsequently, the plasmid which gave a 280 bp DNA fragment containing from the EcoRV site in the vicinity of the 5' side of the UK promoter region originated in pTT04 to the SalI site originated in pUC19 was selected and named as pTT06. The structure of pTT06 was examined by digestion with EcoRV and SacI, and EcoRV and BamHI. pTT06 gave 0.9 kb, 1.8 kb and 2.9 kb fragments by digestion with EcoRV and SacI and 0.6 kb, 1.6 kb and 3.5 kb fragments by digestion with EcoRV and BamHI. These fragments having such sizes were in agreement with the desired ones expected from the restriction enzyme cleavage map of the plasmid.

[III] Introduction into animal cells and establishment of a high-productivity cell strain (i) Materials:

Plasmid DNA

FcεERI/pKC3: The plasmid derived from pKC3 by incorporating the human FcεRIα chain leader sequence and the sFCεRIα chain gene therein. pTT06: The plasmid containing a DHFR gene expression unit place under the control of the UK promoter (5' upstream regulatory region comprising about 8,000 bp and containing the urokinase gene transcription initiation site).

Cells: The cell line CHO DXB-11 (DHFR-deficient strain).

Prepared and multiplied by the method described by G. Urlaub et al. in Proc. Natl. Acad. Sci. USA, 77, 4216–4220 (1980).

Methotrexate (MTX): A 2 mM stock solution was prepared by dissolving (+)Amethopterin (Sigma) in 0.14 M NaCl+0.02 M HEPES (Nacalai Tesque). This solution was added to the cell line medium to a predetermined concentration.

(ii) Procedure (1) DNA introduction and transfectant culture supernatant assay for expression DHFR-deficient CHO DXB-11 cells subcultured using Eagle's MEM-α (ribonucleic acid- and deoxyribonucleic acid-free) supplemented with 10% FCS were detached from the dish by treatment with trypsin (0.25%) and suspended in Hanks' solution to a density of $10^7$ cells/ml. The plasmid DNAs (1 μg of pTT06 and 40 μg of FcεRI/pKC3) were simultaneously introduced into $5 \times 10^6$ cells (0.5 ml of the suspension) by electroporation. After cultivation in Eagle's MEM-α (ribonucleic acid- and deoxyribonucleic acid-free) supplemented with 10% FCS, the resultant colonies were picked and cultured. The spent culture medium of the transfectants was assayed for human sFcεRIα chain activity by the method described below under (2) and strains showing high activity were used for DNA amplification using MTX.

(2) Assaying the soluble human FcεRIα chain

The soluble human FcεRIα chain concentration was determined in terms of the degree of inhibition of binding of $^{125}$I-labeled mouse IgE to FcεRI occurring on a rat basophilic cell line. The materials and procedure used were as follows. (Materials)

Cells: The rat basophil cell line RBL-2H3 (Barsumian, B. L. et al., Eur. J. Immun., 11, 317–323 (1981)) was cultivated in Eagle's MEM containing 10% FCS, 100 U/ml penicillin and 100 μg/ml streptomycin.

IgE: Anti-dinitrophenyl mouse monoclonal IgE (HI-DNP-E-26–82; Liu, F. T. et al., J. Immunol., 124, 2728–2737 (1980)) or anti-trinitrophenyl (TNP) mouse monoclonal IgE was used. The anti-TNP mouse monoclonal IgE was purified from the culture supernatant of the hybridoma IGELb4 (ATCC No. TIB141) or mouse ascitic fluid with the same IGELbH cells.

Iodine-labeling of IgE: The Bio-Rad Enzymobeads method was used. A mixture was prepared from 50 μl of 0.2 M phosphate buffer (pH 7.2), 10 μl of mouse monoclonal IgE (2.14 mg/ml), 50 μl of Enzymobeads reagent, 25 μl of Na$^{125}$I (95 MBq) and 25 μl of a 1% aqueous solution of β-D-glucose. The reaction was carried out at room temperature for 15–20 minutes. After admixing with 150 μl of phosphate-buffered physiological saline containing 10 mg/ml tyrosine, 10% glycerol and 0.1% xylene cyanole, protein recovery was effected by gel filtration using a PD-10 column (Pharmacia).

(Procedure)

IgE binding assay:

1) Since CHO cells are maintained in 10% FCS-supplemented Eagle's MEM-A (ribonucleic acid- and deoxyribonucleic acid-free), samples were prepared by diluting with the same culture medium (125–250 μl).

2) $^{125}$I-Labeled IgE diluted with Dulbecco's phosphate buffered physiological saline supplemented with 3% bovine serum albumin and 0.1% NaN$_3$ (PBS/3% BSA) was added to each sample prepared in 1). The whole volume was 500 μl and the concentration of $^{125}$I-labeled IgE was 100 ng/ml. This mixture was incubated at room temperature for 3–6 hours.

3) To said mixture was added 50 μl of a suspension of RBL-2H3 cells ($3-8 \times 10^7$ cells/ml) in PBS/3% BSA, followed by 1–2 hours of incubation on ice. In an unlabeled IgE group used for assessing nonspecific adsorption of labeled IgE on cells, a mixture of 150 μl of the RBL-2H3 cell suspension and 15 μl of 2.1 mg/ml unlabeled IgE was prepared in advance. This mixture (55 μl) was added to the mixture prepared in step 2).

4) Cells were caused to settle as a sediment by centrifugation (1,000 rpm, 5 minutes) and the supernatant was discarded.
5) The cells were rinsed once with PBS/3% BSA and the bound radio-activity was measured using a gamma counter.
6) The cpm value obtained by adding Eagle's MEM-α (ribonucleic acid- and deoxyribonucleic acid-free) supplemented with 10% FCS was used as a control (the additive-free case) and the percent of binding inhibition was calculated as follows:

$$\text{Binding inhibition (\%)} = \frac{\text{Radioactivity in additive-free case} - \text{Radioactivity in test group}}{\text{Radioactivity in additive-free case} - \text{Radioactivity in IgE-added group}} \times 100$$

(3) Amplification of the inserted gene using MTX

Dishes (10 cm) containing 8–10 ml of a selective medium containing 10 nM MTX were inoculated with a human sFcεRIα chain-producing strain obtained as described in (2) to a density of 5–10×10$^5$ cells/dish. Cultivation was continued for 2–4 weeks while performing medium exchange at intervals of about 3 days. Thereby, a sufficient number of 10 nM MTX-resistant cells were obtained. The cells were transferred to a medium at the next MTX concentration level. In this way, the MTX concentration was increased stepwise for gene amplification, starting from 10 nM MTX, to 50 nM, 100 nM, 200 nM, 500 nM, 1 μM, 2 μM, 4 μM and 10 μM.

(4) Cloning soluble human FcεRIα chain producers

Among the human sFcεRIα chain producers obtained after gene amplification using MTX as described in (3), several strains were subjected to cloning by the limiting dilution method. Thus, cells resistant to each concentration of MTX were cultured in Eagle's MEM-α (ribonucleic acid- and deoxyribonucleic acid-free) supplemented with 10% FCS and 2–10 μM MTX and distributed into the wells of a 96-well plate. Cells were recovered from the wells showing cell proliferation and transferred to a 24-well plate and then, further, to a 10 cm dish. At the stage of confluence, the production of the human sFcεRIα chain in each supernatant was determined. Culture supernatant of 38.4.3 cells in the 24-well plate showed 0.7% of IC$_{50}$. On the assumption that a binding ratio of the human sFcεRIα to IgE was 1:1 in the IgE binding assay, it was calculated that the human sFcεRIα was produced in an amount of 1.8 mg per 1 liter of the culture supernatant of 38.4.3 cells. The yield of the human sFcεRIα of each cell is shown in Table 2.

TABLE 2

| | Yield of human sFcεRI | |
|---|---|---|
| Clone | Supernatant in 24-well plate* (mg/l) | Supernatant in 10 cm-dish* (mg/l) |
| 38.4.2 | 1.6 | 4.0 |
| 38.4.3 | 1.8 | 4.5 |
| 58.2.8 | 1.3 | 3.9 |
| 56.2.7 | 1.7 | 5.1 |
| 66.2.2 | 1.5 | 4.4 |
| 19.10.23 | 2.1 | 4.6 |

*:Average of the amounts of the product from the culture supernatant in two different concentrations.

[IV] Purification of the human sFcεRIα chain

To 983 ml of the culture supernatant derived from a cloned cell strain 38.4.3 showing a relatively high production of the human sFcεRIα chain was added a 1/20 volume of 1 mM Tris, pH 8.0, together with 10 mM benzamidine, 10 mM ethylenediaminetetraacetic acid and 0.02% sodium azide. The mixture was filtered (0.22-μm filter) and the filtrate was purified using an IgE-Sepharose 4B column [prepared by binding 10 mg of anti-trinitrophenyl IgE purified from a mouse hybridoma IGELb4 (ATCC No. TIB141) culture supernatant to 1 g of activated CH Sepharose (Pharmacia) in 0.1 M sodium hydrogen carbonate]. The column was washed with PBS containing 0.02% sodium azide. The protein bound to the column was eluted with an eluant comprising 0.2 M acetic acid, 0.2 M sodium chloride and 0.02% sodium azide, pH 2.8. The thus purified human sFcεRIα chain was dialyzed against 10 mM ammonium hydrogen carbonate, and 200 μl of the dialyzate was dried in SpeedVac and checked by SDS electrophoresis. Upon staining with Coomassie Brilliant Blue, a distinct band was detected at a position corresponding to a molecular weight of about 50 kDa, without any other protein band, under reducing conditions as well as under nonreducing conditions (FIG. 4). This protein had an activity of inhibiting the binding of radio-labeled IgE to basophilic cells (RBL-2H3 cells; vide supra). The concentration of such purified human FcεRIα chain was determined by the method of Bradford [Bradford, M. M., Anal. Biochem., 72, 248 (1976)].

EXAMPLE 2

Composition for administration by injection or spraying

In distilled water for injection were dissolved 100 mg of the purified human sFcεRIα and 100 mg of glucose to give a purified human sFcεRIα concentration of 2 mg/ml. The solution was filtered using a 0.45-μm membrane filter and the filtrate was aseptically distributed into 5-ml vials, followed by nitrogen gas charging and tight closure to give a composition for intravenous injection or for spraying.

EXAMPLE 3

Ophthalmic solution

In distilled water for injection were dissolved 500 mg of the purified human sFcεRIα, 50 g of sorbitol and 20 mg of methyl parahydroxybenzoate. The pH was adjusted to 6.5 with a phosphate buffer and the whole volume was made to 1,000 ml. The solution was filtered using a 0.45 μm membrane filter and the filtrate was aseptically distributed into eye drop bottles. Thus was prepared an ophthalmic solution.

EXAMPLE 4

Composition for nasal administration

A composition for nasal administration was prepared in the same manner as in Example 3.

EXAMPLE 5

Ointment

To 25.0 parts by weight of a 2% aqueous solution of a carboxyvinyl polymer (Carbopol 940, product of Goodrich) was added gradually 25 parts by weight of a 2% aqueous solution of sodium hydroxide with stirring. Further stirring gave a gel-like composition.

A solution of 2 parts by weight of the purified human sFcεRIα in an appropriate amount of purified water was added to the gel-like composition, followed by further addition of purified water to make the whole amount 100 parts by weight. Subsequent uniform stirring gave an ointment.

EXAMPLE 6

Ointment

White petrolatum (60 parts by weight), 1 part by weight of polyoxyethylene cetyl ether and 1 part by weight of aluminum stearate were melted and mixed under heating. While maintaining the mixture at about 75° C., 5 parts by weight of sorbitan monostearate and 10 parts by weight of purified water were added thereto. The mixture was stirred and then cooled to about 45° C. and 5 parts by weight of the purified human sFcεRIα in an appropriate amount of purified water was added thereto. The subsequent stirring gave an ointment.

TEST EXAMPLE 1
Effect on anaphylactic shock in actively sensitized rats

The test was performed by the method of Levine et al. [Levine, B. B. et al., Int. Arch. Allergy Appl. Immunol., 39, 156 (1979)]. ICR rats were sensitized by intraperitoneal administration of a solution of 10 μg of DNP-Ascaris in an Al(OH)$_3$ gel (2 mg/ml). Four weeks after sensitization, the animals were given the human sFcεRIα-containing injection prepared as described above in Example 1 by intravenous injection two times at a dose of 100 μg/kg/day. Twenty-four hours after administration, anaphylactic shock was induced by intravenous administration of DNP-ovalbumin (10 mg/kg) and animal deaths within 24 hours were counted (n=5). While 4 animals died in the control group, no animals died in the human sFcεRIα group.

TEST EXAMPLE 2
Effect on allergic conjunctivitis in mice

BALB/C mice were sensitized by intraperitoneal administration of a solution of 10 μg of DNP-Ascaris in a 2 mg/ml Al(OH)$_3$ gel. Four weeks following sensitization, 0.1 ml of the ophthalmic solution prepared as described above in Example 3 was administered to each eye by instillation once daily for a week. On the next day, 0.1 ml of a 0.5% DNP-ovalbumin solution was instilled in each eye. While hyperemia and edema of the ocular conjunctiva, namely signs of conjunctivitis, were observed in the control group of mice, no such signs were observed in the group of mice given human sFcεRIα. Administration of the above-mentioned ophthalmic solution by instillation to the control group mice that had showed such symptoms as mentioned above ameliorated the symptoms.

TEST EXAMPLE 3
Effect on atopic dermatitis

The ointment prepared as described above in Example 5 was applied once daily to the rough skin of pediatric patients with atopic dermatitis. After several weeks of application, the rough skin began to return to normal, with the itchy sensation subsiding. Application of the ointment did not cause any observable signs of skin irritation, for example rash.

TEST EXAMPLE 4
Inhibition of bronchial constriction in actively sensitized guinea pigs Evaluation was performed by the Konzett-Rossler method [H. Konzett and R. Rossler: Naunyn-Schmiedbergs Arch. Pharmakol., 195, 71 (1940)]. Male Hartley guinea pigs were sensitized with ovalbumin (50 mg/kg, intraperitoneal administration). Fourteen days later, the guinea pigs were anesthetized with pentobarbital (70 mg/kg, intraperitoneal administration) and their spontaneous respiration was arrested using succinylcholine (2 mg/kg, intraperitoneal administration). The trachea of each animal was cannulated and respiration was maintained under a positive pressure using a small-sized artficial respirator (5 ml/breath, 87 breaths/minute, 10 cm water). The constrictive response of the bronchus was expressed in terms of the amplified mobile area of tracing on a physiological recorder of the outflow of air into the lung as measured by an air flow meter connected in series with a differential pressure transducer. The human sFcεRIα-containing composition for injection as prepared in Example 1 was intravenously administered at a dose of 50 μg/kg. An hour later, ovalbumin was intravenously administered (300 μg/kg). It was found that administration of human sFcεRIα significantly inhibited the constrictive response of the bronchus in the guinea pigs.

TEST EXAMPLE 5
Inhibition of the passive cutaneous anaphylaxis (PCA) response in rats Spraque-Dawley rats (4–8 weeks old) were sensitized by intracutaneous injection of mouse IgE anti-TNP antibody which was produced by hydridoma IGEL b4 (ATCC TIB141) into the shaven back skin of the rats (10 ng in 50 μl PBS/site). The serially diluted human sFCεRIα was injected into the animals intravenously (50 μg/kg, 500 μg/kg and 5 mg/kg) at 6 hours after IgE sensitization. The animals were intravenously challenged with TNP-HSA (0.5 mg) solution containing 1% Evans blue at 24 hours after IgE sensitization. After 30 minutes, the PCA response (IgE inhibition (%)) was determined by measuring the dye concentration in the extracts of the skin lesions in accordance with the method described in Hirada, M. et al., J. Pharm. Pharmac., 23, 218 (1971).

As a result, it was found that the groups given 50 μg/kg, 500 μg/kg and 5 mg/kg of human sFCεRIα showed IgE inhibition of 0%, 22% and 89%, respectively.

While the invention has been described in detail and with reference to specific embodiments thereof, it will be apparent to one skilled in the art that various changes and modifications can be made therein without departing from the spirit and scope thereof.

What is claimed is:

1. A method of preventing an allergic response selected from the group consisting of anaphylactic shock, pollen allergy, atopic dermatitis and bronchial asthma in a human, which method comprises, administering to said human prior to onset of said allergic response and prior to a stage where IgE concentration is elevated, an antiallergic composition which comprises, as an active ingredient, a peptide having a portion of an amino acid sequence of SEQ ID NO. 1, said peptide being capable of binding to human IgE and which contains a soluble IgE binding fragment of a high affinity immunoglobulin E receptor α-chain of human origin.

2. The method of preventing an allergic response of claim 1, wherein said peptide is administered at a dose of at least twice the amount of IgE corresponding to an exogenous factor.

3. The method of claim 1 wherein the peptide is administered in an amount of at least twice the amount of the peptide needed for binding to the expected amount of increase of IgE caused by the allergic response.

4. The method of claim 1 wherein the peptide is administered in at least the amount of the peptide needed for binding $10^{12}$ to $10^{14}$ molecules of IgE per ml of blood serum of the patient.

5. The method of claim 1 wherein the peptide is administered in at least a dosage of 500 µg/kg of patient weight.

6. The method of claim 1 wherein the anti-allergic composition is administered systemically.

7. The method of claim 1 wherein the anti-allergic composition is administered topically.

* * * * *